US010456316B2

(12) United States Patent
Popovic et al.

(10) Patent No.: US 10,456,316 B2
(45) Date of Patent: Oct. 29, 2019

(54) ACTUATORS AND METHODS OF USE

(71) Applicant: Worcester Polytechnic Institute, Worcester, MA (US)

(72) Inventors: Marko Popovic, Somerville, MA (US); Cagdas Onal, Allston, MA (US); Daniil Effraimidis, Worcester, MA (US); Brian Jennings, Danbury, CT (US); Gregory D. McCarthy, Lumberton, NJ (US); Nicholas Corso, Walden, VT (US)

(73) Assignee: Worcester Polytechnic Institute, Worcester, MA (US)

( * ) Notice: Subject to any disclaimer, the term of this patent is extended or adjusted under 35 U.S.C. 154(b) by 787 days.

(21) Appl. No.: 14/628,663

(22) Filed: Feb. 23, 2015

(65) Prior Publication Data

US 2015/0359698 A1 Dec. 17, 2015

Related U.S. Application Data

(60) Provisional application No. 62/011,830, filed on Jun. 13, 2014.

(51) Int. Cl.
*A61H 3/00* (2006.01)
*A61H 1/00* (2006.01)
(Continued)

(52) U.S. Cl.
CPC ............ *A61H 3/00* (2013.01); *A61F 2/68* (2013.01); *A61H 1/024* (2013.01); *A61H 1/0277* (2013.01);
(Continued)

(58) Field of Classification Search
CPC .. A61H 3/00; A61H 1/00; B25J 9/1075; B25J 9/142; F15B 15/103; F15B 15/06; F01B 19/04
See application file for complete search history.

(56) References Cited

U.S. PATENT DOCUMENTS 4,777,868 A * 10/1988 Larsson ................ F15B 15/103
92/42
4,819,547 A * 4/1989 Kukolj .................. F15B 15/103
92/153

(Continued)

OTHER PUBLICATIONS

PCT International Search Report and Written Opinion issued in International Application No. PCT/US2015/017114 dated May 21, 2015.

*Primary Examiner* — Timothy A Stanis
(74) *Attorney, Agent, or Firm* — Greenberg Traurig, LLP; Roman Fayerberg

(57) ABSTRACT

Actuators and methods of use are provided. An actuator may include an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state, wherein the movement of the actuator between the relaxed state and the expanded state causes a movement of a structure to which the actuator is attached.

20 Claims, 19 Drawing Sheets

(51) Int. Cl.
    F15B 15/10      (2006.01)
    A61H 1/02       (2006.01)
    A61F 2/68       (2006.01)
    A61F 2/74       (2006.01)
    A61F 2/50       (2006.01)
    A61F 2/70       (2006.01)
    A61F 2/76       (2006.01)
(52) U.S. Cl.
    CPC ......... *A61H 1/0281* (2013.01); *F15B 15/103*
          (2013.01); *A61F 2002/5066* (2013.01); *A61F
          2002/704* (2013.01); *A61F 2002/74* (2013.01);
              *A61F 2002/745* (2013.01); *A61F 2002/748*
            (2013.01); *A61F 2002/762* (2013.01); *A61F
              2002/7635* (2013.01); *A61H 2201/1238*
              (2013.01); *A61H 2201/164* (2013.01); *A61H
                2201/165* (2013.01); *A61H 2201/1614*
              (2013.01); *A61H 2201/1635* (2013.01); *A61H
                2201/5007* (2013.01); *A61H 2201/5058*
              (2013.01); *A61H 2201/5071* (2013.01); *A61H
                                   2201/5087* (2013.01)

(56)              References Cited

U.S. PATENT DOCUMENTS 4,832,473 A      5/1989  Ueda
    5,083,498 A *    1/1992  Sato ................... F15B 15/125
                                                         73/731
    5,218,280 A *    6/1993  Edwards ................. B25J 9/142
                                                         318/567
    5,662,693 A *    9/1997  Johnson .................. A61F 5/01
                                                         607/48
    6,168,634 B1     1/2001  Schmitz
    6,532,400 B1 *   3/2003  Jacobs ................. B25J 9/1075
                                                       318/568.11
    6,592,533 B1 *   7/2003  Yonekawa ............... A47C 4/54
                                                         601/148
    6,689,074 B2     2/2004  Seto et al.
    6,741,911 B2 *   5/2004  Simmons ............... B25J 9/0006
                                                       318/568.11
    7,413,554 B2 *   8/2008  Kobayashi ............ A61F 5/0102
                                                         602/13
    7,725,175 B2 *   5/2010  Koeneman ............... A61H 1/02
                                                         600/546
    8,307,753 B2    11/2012  Woods et al.
    8,597,212 B2 * 12/2013  Kawakami .............. A61F 5/013
                                                         601/23
    8,696,604 B2 *   4/2014  Kawakami ............ A61F 5/0123
                                                         601/23
    2001/0029343 A1 10/2001  Seto et al.
    2007/0144299 A1*  6/2007  Okazaki ............... B25J 9/1075
                                                         74/490.1
    2009/0314119 A1* 12/2009  Knoll ................ A61B 1/00156
                                                        74/490.01
    2011/0118635 A1*  5/2011  Yamamoto ............... A61H 1/02
                                                          601/5

* cited by examiner

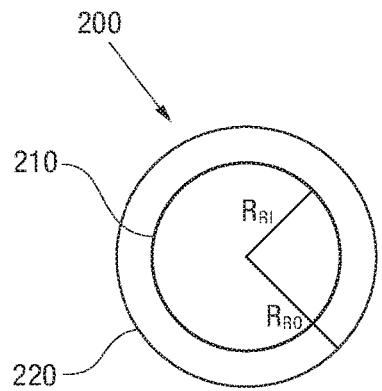 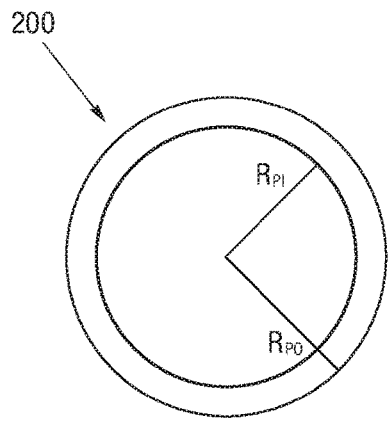
FIG. 2C    FIG. 2D
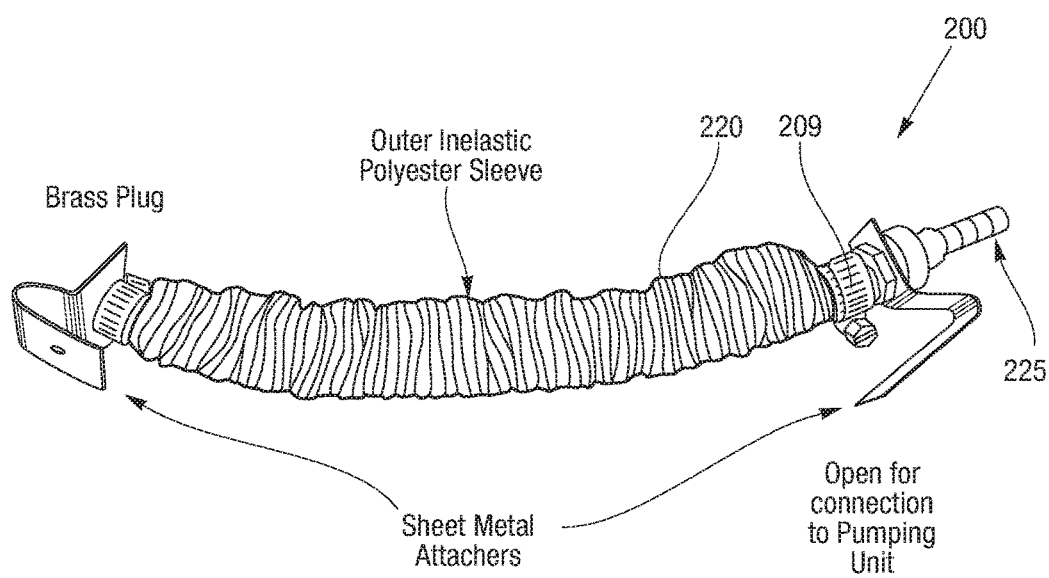
FIG. 2E

FIG. 2F (ii) 
FIG. 2F (iii) 
FIG. 2F (iv) 

FIG. 2G (ii) 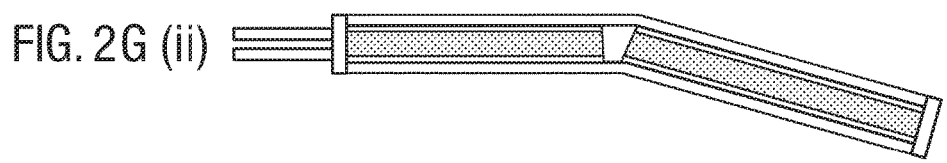

FIG. 3A(ii)

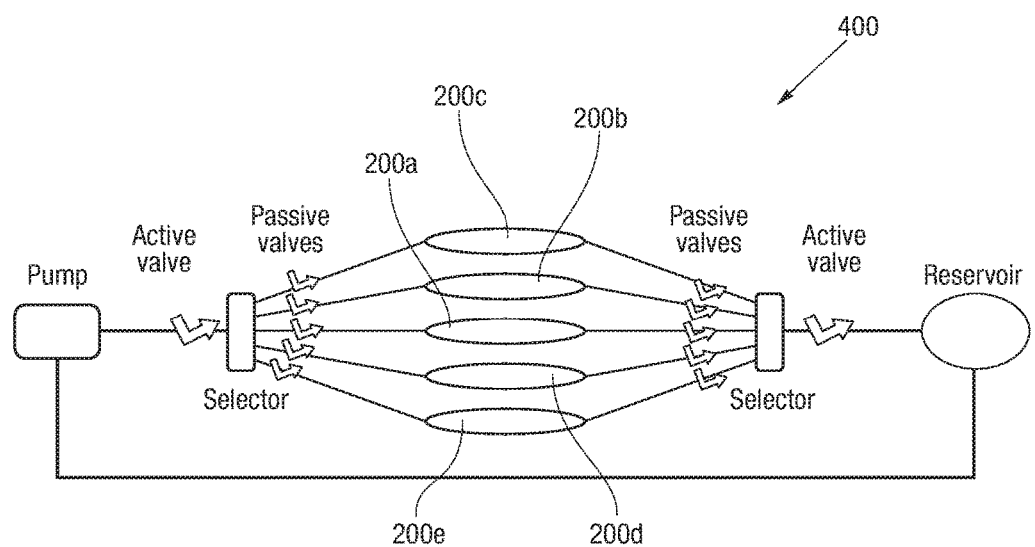
FIG. 5A
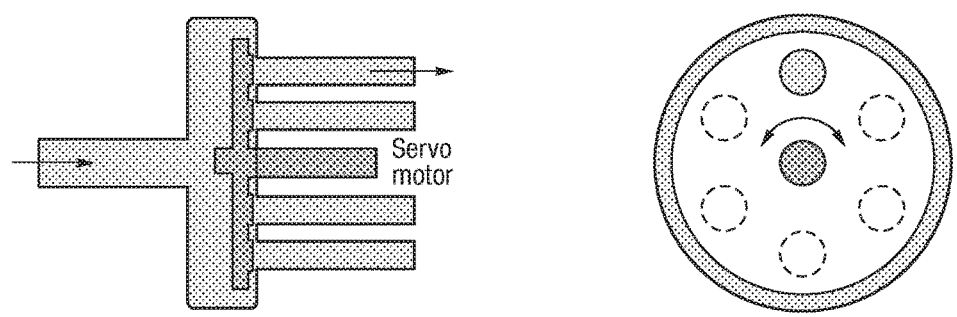
FIG. 5B (i)    FIG. 5B (ii)

FIG. 7A (iii)

ically actuated Exo-Musculature, consisting of a network of actuator, that can be rapidly assembled, integrated with desired artificial skeleton and utilized as stand-alone robotic system.

ACTUATORS AND METHODS OF USE

RELATED APPLICATIONS

This application claims the benefit of and priority to U.S. Provisional Application No. 62/011,830, filed on Jun. 13, 2014, and which is incorporated herein by reference in its entirety.

FIELD

The present disclosure relates to hydraulic actuators for medical applications and general robotics applications.

BACKGROUND

There is a wide array of muscular degenerative disorders that affect millions of people worldwide every year. The most common type of muscular dystrophy, Duchenne muscular dystrophy, occurs in 1 of every 3300 male births. In addition, stroke, the leading cause of serious, long term disability in the United States, affects 795,000 people each year. Finally, the elderly population (65 and older) in the United States was 40.3 million in 2010, which was 13% of the total population. This number continues to grow and the elderly are predicted to comprise of 20% of the population of the United States by 2050. Many of these individuals cannot complete the simplest of tasks which require precise movement of arms, legs, and all other skeletal muscle extremities.

There is a demand for a hydraulically actuated exo-musculature that can be used to promote muscular rehabilitation, while allowing the user to wear the device comfortably with the body's natural movement in mind. A fully functional and comprehensive exo-musculature has the potential to provide assistive movement for entire human body by replacing the often cumbersome and limiting traditional robotic system. Still further, the hydraulically actuated Exo-Musculature, consisting of a network of actuator, that can be rapidly assembled, integrated with desired artificial skeleton and utilized as stand-alone robotic system.

SUMMARY

Hydraulic actuators and methods of their use are disclosed. According to some aspects of the present disclosure, there is provided a hydraulically operated lattice device comprising a first member; a second member; and an actuator connected to the first member at its first end and to the second member at its second end, the actuator comprising an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state, wherein the movement of the actuator between the relaxed state and the expanded state cause a movement of at least one of the first member and the second member relative to the other member.

According to some aspects of the present disclosure, there is provided an actuator system comprising a reservoir including an actuating fluid; and multiple actuators, each of the multiple actuators comprising: an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state; a pump in fluid communication with the reservoir and the actuators for selectively supplying the actuating fluid to the actuators; and a controller in communication with the pump to control operation of the pump.

According to some aspects of the present disclosure, there is provided an exoskeleton joint comprising a wearable sleeve; a first member and a second member combined with the wearable sleeve, the second member being pivotably connected to the first member by a hinge; an actuator connected to the first member at its first end and to the second member at its second end, the actuator comprising: an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state, wherein the movement of the actuator between the relaxed state and the expanded state cause a movement of at least one of the first member and the second member relative to the other member.

DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 2C and FIG. 2D show a cross section of an actuator in a relaxed state and an expanded state according to the present disclosure;

FIG. 2E illustrates an embodiment of a actuator according to the present disclosure;

FIG. 5A, FIG. 5B(i), FIG. 5B(ii)

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The present disclosure provides a new type of an actuator or a hydraulic actuator that can be made very similar in size, mass and overall performance to biological muscles. The actuator of the present disclosure can be produced very inexpensively and can have a variety of applications from wearable medical devices to stand-alone robotics systems. The actuators of the present disclosure can be used in a different industries and technologies, such as, for example, the health industry, medical device technologies for humans and animals, space technologies, underwater technologies, robotic system technologies and similar industries and technologies.

Figure 1:
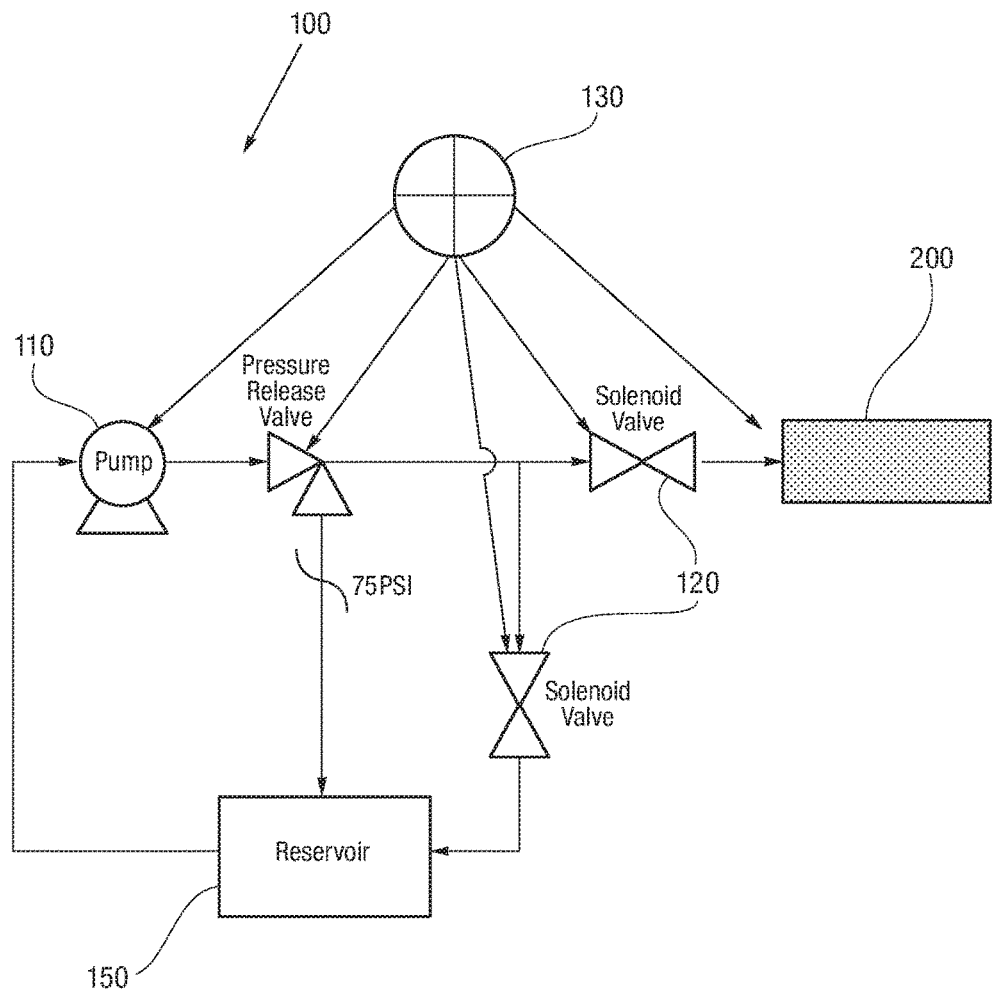
FIG. 1 is illustrates an actuator system according to the present disclosure.

In reference to FIG. 1, an actuator system 100 may include a pump 110, one or more valves 120, a controller 130 and one or more elastic actuators 200 that can act as an artificial muscle. The actuator system 100 may further include a reservoir 150 for a fluid used to actuate the elastic actuator. In operation, the pump may be used to pump the actuating fluid from the reservoir into the artificial actuator to pressurize and expand the actuator, thus providing a pushing force. Once a desired pressure is achieved, the actuator may be maintained at the desired pressure, providing full control of the actuation. When the fluid is discharged from the elastic actuator, the pressure release from the actuator causes the actuator to contract, providing a pulling force. The controller 130 is in communication with the component of the actuator system 100, as shown in FIG. 1, to control the operation of the actuator system 100. The controller can be any type of controller known and used in the art.

Figure 2A:
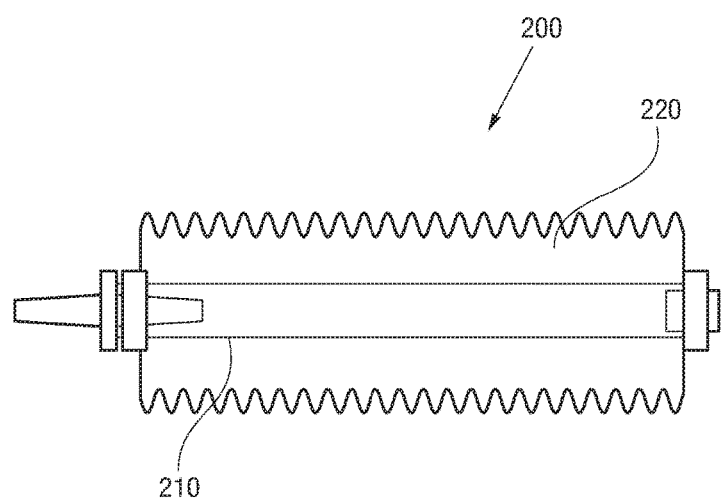
FIG. 2A illustrates an actuator according to the present disclosure in a relaxed state.
Figure 2B:
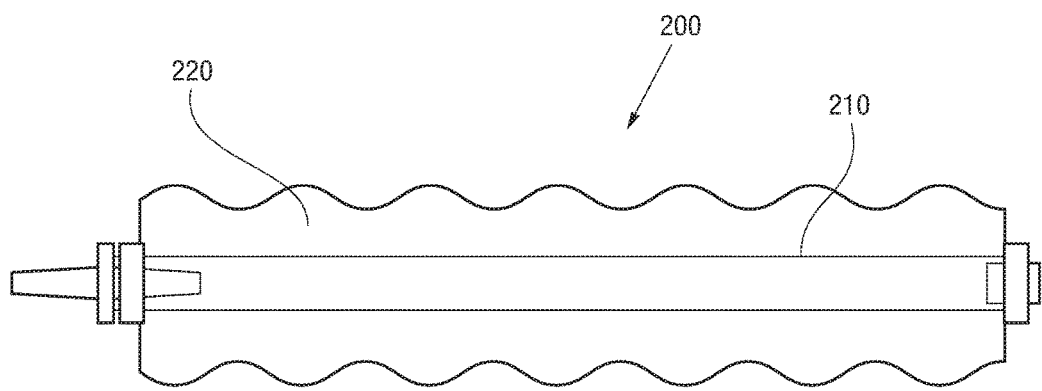
FIG. 2B illustrates an actuator of the present disclosure in an extended state.

In reference to FIG. 2A and FIG. 2B, in some embodiments, the actuator 200 includes an inner member 210 surrounded by an outer member 220. In some embodiments, the inner member 210 forms an elongated, expandable compartment for receiving an actuating fluid. The inner member 210 can thus be moved from a relaxed state to an expanded or pressurized state by introducing the actuating fluid into the inner member 210 and back to the relaxed state upon discharge of the actuating fluid from the inner member 210. In this manner, the contracting movement of the inner member 210 can be used as an actuating force. The inner member 210 may be made of various medical grade expandable materials, preferably having one or more of the following characteristics: resistance to wear and tear, high tensile strength, resilience, and elongation.

FIG. 2C and FIG. 2D show a cross section of inner member 210 for at least one geometry embodiment. For example, FIG. 2C shows a relaxed actuator inner and outer radius and FIG. 2D shows a pressured actuator inner and outer radius. As can be seen from these figures, the inner member 210 initially expands in both the radial and longitudinal direction. In fact, at the start of the expansion, the radial expansion may be greater than the longitudinal expansion. However, as the pressure inside the inner member increases with addition of the actuating fluid and the inner member 210 continues to expand, it gets to the point when the longitudinal expansion become dominant, until the inner member 210 can no longer expand radially at all, and only continues to expand in the longitudinal direction. This can lead the actuator to produce a non-linear force. To combat this, in some embodiments, the actuator 200 may be designed to reduce, if not completely prevent, the radial expansion of the inner member 210. In some embodiments, the inner member 210 may be pressurized to a pressure sufficient to fully radially expand the inner member 210, such that any additional pressurization of the inner member 210 may result in longitudinal extension only.

Referring to FIG. 2C and FIG. 2D, tensile strength is product of tensile stress and wall cross sectional area. For small pressures of actuating fluid the wall area may be treated constant. Hence, for specified inner and outer wall radii of relaxed inner member and for specified radius of radially constraining non-stretchable outer layer the inner radius or pressurized inner member, treated as constant, can be obtained. The inner radius of pressurized inner member can be then used to estimate the inner cross sectional area subject to pressure generated by the actuating fluid; given the pressure of actuating fluid, that can be obtained with conventional pressure sensor, the force produced by pressure of actuating fluid can be estimated as pressure times estimated inner tube area.

Still referring to FIG. 2A, FIG. 2B, FIG. 2C and FIG. 2D, the actuator 200 can both pull and push. When an elastic contractile force is due to elongation of an inner member 210 is larger than a force produced by pressure of an actuating fluid, then the actuator 200 is pulling. On the other hand, when the force produced by pressure of an actuating fluid is larger than an elastic contractile force due to the elongation of an inner member 210, then the actuator is pushing. This can remove the necessity for an antagonistic pairing configuration, meaning that a joint can be fully actuated by a single actuator, which can both push and pull.

Desired ranges of elongation and tensile strength of the actuator 200 may vary depending on application. For example, in some large strain applications, the elongation can include ranges up to hundred percent or more of the actuator's relaxed length, such as, when the actuator's end points are attached further away from the joint axis. For some small strain applications, the elongation may include ranges of a few percent of the actuator's relaxed length, such as when the actuator's end points are attached closer to the joint axis. Similarly, tensile stress, being a product of Young's modulus and strain may vary many orders of magnitude depending on the application. Young's modulus of the actuator can depend on Young's modulus of the inner member material(s), in addition to the number of materials used per embodiment. For example, there can be single material embodiments or there may be several materials used for other embodiments. In the multiple material embodiments, various materials can contribute to a composite Young's modulus. For example strips of the same or different materials may be added centrally or on a side along the actuator length to reinforce actuator strength and/or introduce different dynamical performance, as well as geometry of the inner member. In some embodiments, this may depend on the inner and outer radius of the inner member wall, whereas in other embodiments, this may depend on details of more complex, possibly composite geometry.

In some embodiments, the inner member 210 may be made from latex. For example, latex has a very high efficiency because latex can have a very small elastic hysteresis. This means that only a very small amount of energy (on the order of only a few percent per duty cycle) is dissipated due to material inner friction.

The outer member 220 may form an outer sleeve around the inner member 210 to direct the expansion and contraction of the inner member 210. The outer member 220 may be made of a variety of different materials, preferably having one or more of the following characteristics: cloth like inelastic but foldable, tough, with low absorption of moisture and a high flexural linear strength. In some embodiments, the outer member 220 may be made of polyester. In some embodiments, the outer member 220 may be configured to expand only in the longitudinal direction. In some embodiments, the outer member 220 may be made of an inelastic material with wrinkles or folds. In this manner, the outer member 220 may be folded when the inner member 210 is in the relaxed state. However, as the inner member 210 is expanded with actuating fluid, the outer member 220 would begin to stretch-out in the longitudinal direction until the outer member 220 is fully expanded. In some embodiments, the outer member 220 may only be connected to the inner member 220 at the ends, but not along entire lengths, to allow the outer member 220 to freely fold and expand, as required. In some embodiments, the outer member 220 is connected to the inner member 210 discontinuously, that is, at certain one or more contact points, in addition to end points rather than along the entire length. This may further aid in folding and unfolding of the outer member 220.

The outer member 220 may be designed to prevent or at least minimize radial expansion of the inner member 210. To that end, it is desirable that when the outer member 220 is expanded there are no openings in the outer member 220 through which the inner member 210 can protrude in radial direction when pressurized. Allowing parts of the inner member 210 to protrude through the outer member 220 may jeopardize the efficiency of the system as energy would be transferred not along actuation dimension, i.e., longitudinal direction, but in a radial direction. Moreover, if the inner member 210 protrudes through the outer member 220, the inner member 210 may be pinched by or become entangled with the outer member when contracted, which may cause further problems. Accordingly, in some embodiments, the outer member 220 can be made from a sheet of material which in the expanded state has no openings to provide an unbroken or uninterrupted barrier which prevents the inner member 210 from protruding through the outer member 220, in whole or in part. By way of a non-limiting example, the outer member 220 may be made from a corrugated fabric or cloth like material. The expansion of such outer member 220 is not likely to create any openings in the outer member 220 through which the pressurized inner member 210 may protrude, in whole or in part. The outer member 220 is allowed to expand by unfolding the folds of the outer member 220, rather than by simply stretching the outer member 220, which may result in unwanted openings.

In some embodiments, the inner member 210 may include two or more members and the outer member 220 may include two or more members, or some combination of one or more inner members 210 with one or more outer members 220. For example, it is contemplated there could be several inner members 210 for a single outer member 220, such as the several inner members 210 acting as actuator fibers within the same actuator 220. It is also contemplated that there could be several actuators 220 configured in parallel.

FIG. 2E shows an embodiment of the actuator 200, wherein the prototype actuator 200 includes an outer inelastic member 220, fasteners 209 to attach the actuator to a joint, and a fluid adaptor 225 used for accessing the actuating fluid to into the inner member 210 (not visible). The actuator 200 may include at least one brass plug located at an end of the prototype actuator 200 to plug one end of the actuator 200.

The actuator 200 may have segments with variable elastic properties, different cross sections or both along its length. This may be achieved by changing the elastic properties of the inner member 210, outer member 220 or both. In some embodiments, the actuator can have variable elastic properties as a function of azimuthal angle. For example, one side of the inner member 210 may have different elastic property than the other side (such as due to reinforcement). In this manner, pressurizing the actuator 200 with actuating fluid can cause the actuator 200 to curve.

Figure 2F:
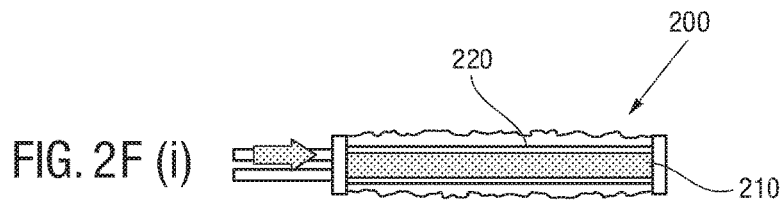
FIG. 2F(i)-FIG. 2F(v) show an axially symmetric actuator according to the present disclosure.
Figure 2F:
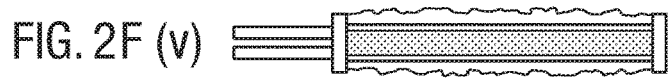
Figure 2G:
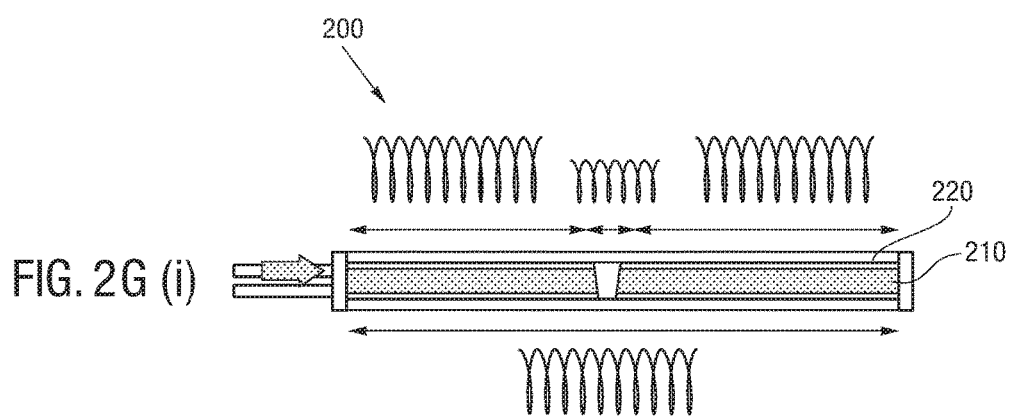
FIG. 2G(i) and FIG. 2G(ii) show an axially asymmetric actuator according to the present disclosure.

As shown in FIG. 2F(i)-FIG. 2F(v), in some embodiments, the actuator 200 may be axially symmetric in its elastic properties. An axially symmetric actuator may be able to expand and contract substantially linearly substantially in longitudinal direction, without bowing. As shown in FIG. 2G(i) and FIG. 2G(ii), the actuator 200 may be axially asymmetric in its elastic properties, with different sections of the actuator 200 having different elasticproperties. An axially asymmetric actuator may bow when pressurized as shown in FIG. 2G(i) and FIG. 2G(ii). In some embodiments, the elastic properties of the actuator 200 may be designed such that the actuator 200 is axially asymmetric and conforms to more complex pre-defined shapes.

It should, however, be noted that due to inherent elasticity of the actuator 200, even an axially symmetric actuator may experience some curving when pressurized. In some embodiments, when bowing is not desirable, an additional non-stretchable layer may be added to the actuator 200 to diminish or eliminate bowing of the actuator 200 and instead to guide expansion of the actuator along a substantially straight line. Alternatively or additionally, the inner member, the outer member or both can be reinforced.

Figure 2H:
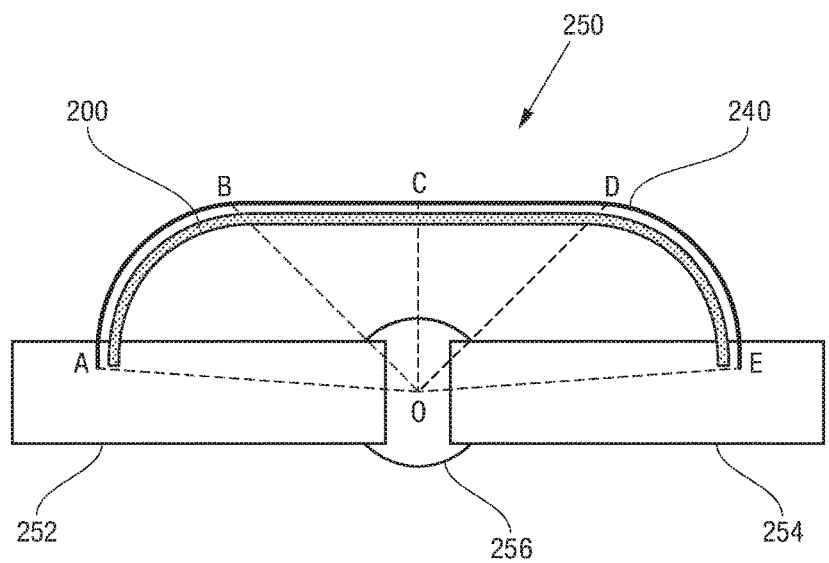
FIG. 2H, FIG. 2I, FIG. 2J and FIG. 2K show various embodiments of a lattice device including an actuator according to the present disclosure.
Figure 2I:
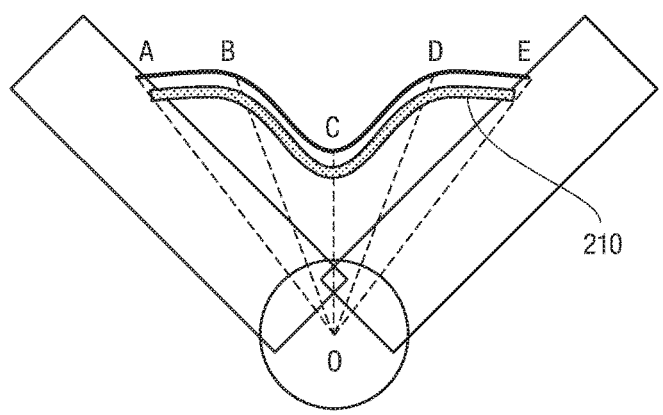

FIG. 2H and FIG. 2I illustrate a lattice device 250 operated by the actuator 200. The lattice device 250 may include a first member 252 and a second member 254 pivotally connected to one another by a hinge or joint 256. The members 252, 254 may be made of a rigid or semi-rigid material, and may be made of different shapes. In some embodiments, the members 252, 254 may be an elongated rod. The lattice device 250 may be operated (bended and straightened) by the actuator 200, which may be connected at its opposite ends to the first member 252 and the second member 254. In some embodiments, the lattice device may be configured so only one of the members moves relative to the other member. In some embodiments, the lattice device may be configured that both members 252, 254 move relative to one another.

As shown in FIG. 2H, the actuator 200 may be shaped to a desired shape to aid in operating the lattice device 250. The actuator 200 may also be allowed to bow in a pre-defined manner to increase the force that the actuator can apply on the first and second members 252, 254. In some embodiments, this can be achieved using an axially asymmetric actuator or multiple actuators, as discussed above. Alternatively or additionally, this may be achieved by providing a restraining member 240, which may be designed to guide the bowing of the actuator 200. Segments AB, BC, CD, DE of the restraining member or of the actuator can be constructed from different materials characterized by different stiffness or pre-stretched wrinkling level. In some embodiments, the segments AB and DE may be designed so the angles at points A and E (connection points of the actuator to the lattice) may be approximately 90 degrees or as close to 90 degrees as practical or possible. This may enable the actuator 200 to apply more torque on the members 252, 254 of the lattice with same actuator force compared to if there was no bowing or too much bowing. In this manner, the efficiency of the actuator may be improved, and the actuator may be allowed to perform tasks such as pushing larger loads. At the same time, the segments BC and CD may be designed to provide controlled bowing of the actuator along those segments.

Figure 2J:
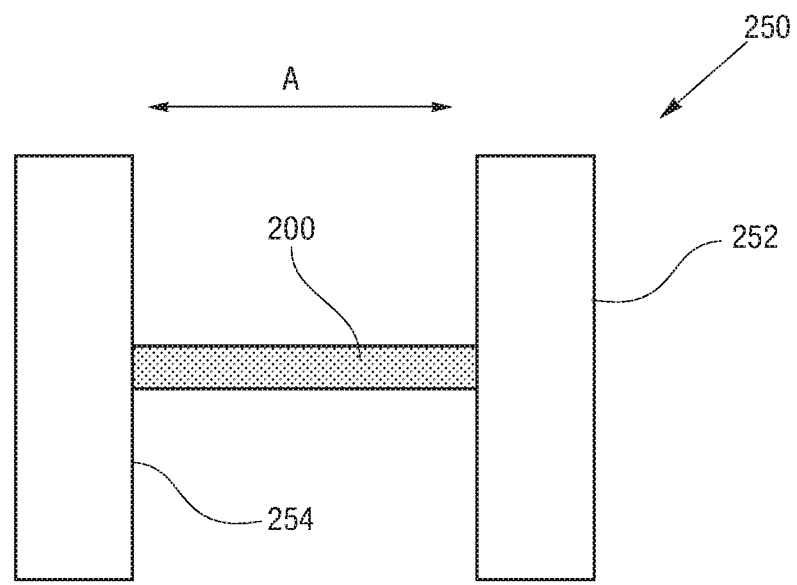
Figure 2K:
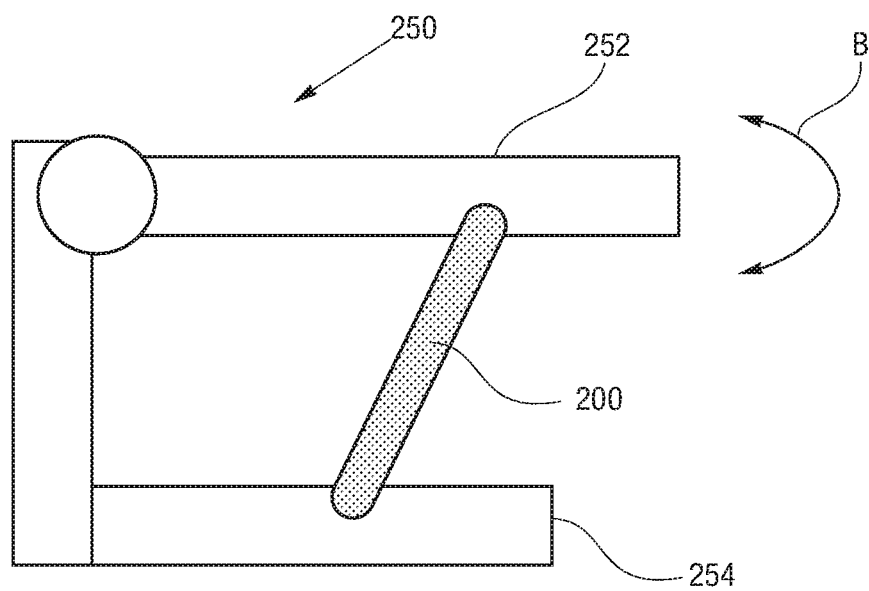

FIG. 2J and FIG. 2K illustrate alternative embodiments of the lattice device 250. As shown in FIG. 2J, the actuator 200 can move the members 252, 254 linearly relative to one another as indicated by the arrow A. As shown in FIG. 2K, in some embodiments, the members 252, 254 may be connected by a series of additional members, joints or both to allow the movement of the member 252 relative to the member 254 in a manner indicated by the arrow B.

Referring back to FIG. 1, various pumps can be used in the actuator systems 100 of the present disclosure. In some embodiments, a diaphragm pump can be used. By way of a non-limiting example, SHURflo 8035-963-239 12 VDC diaphragm manual demand pump may be used. It is a positive displacement, 3-chamber diaphragm pump that utilizes maximum discharge pressures to deliver high flow rates. The check valve is 2-way operational and prevents reverse flow while providing 6 ft head of forward flow. The actuator system of the present disclosure may further include various valves and sensors for controlling the flow and pressure of the actuating fluid. In some embodiments, solenoid valves may be used.

Figure 3A:
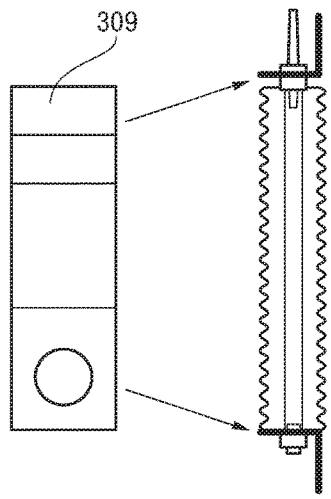
FIG. 3A(i) and FIG. 3A(ii) illustrate a lattice device including an actuator according to the present disclosure.
Figure 3B:
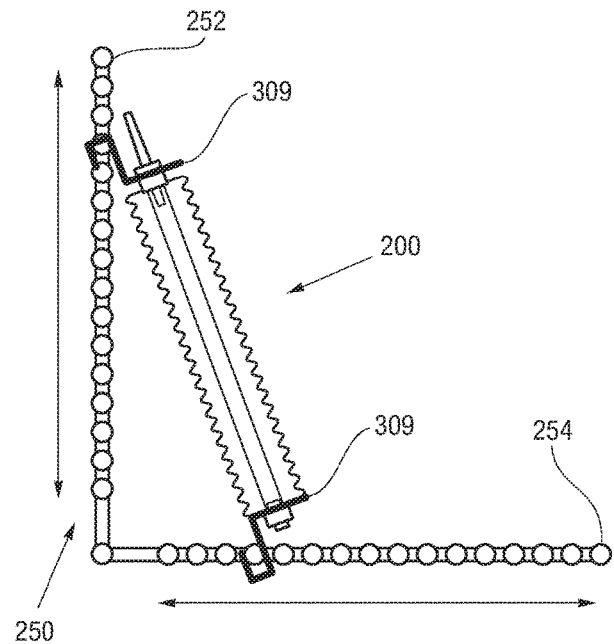
FIG. 3B and FIG. 3C shows an example of use of a lattice device according to present disclosure.
Figure 3B:
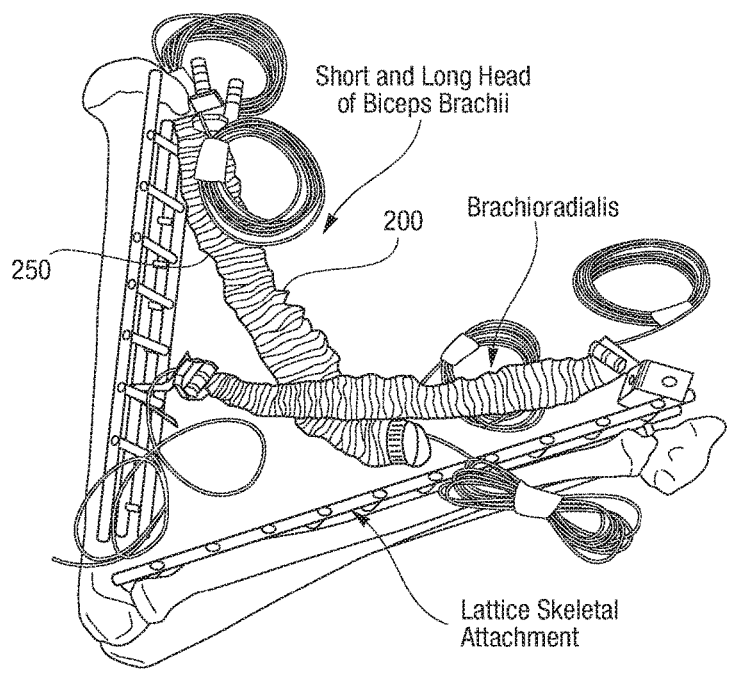
Figure 3C:
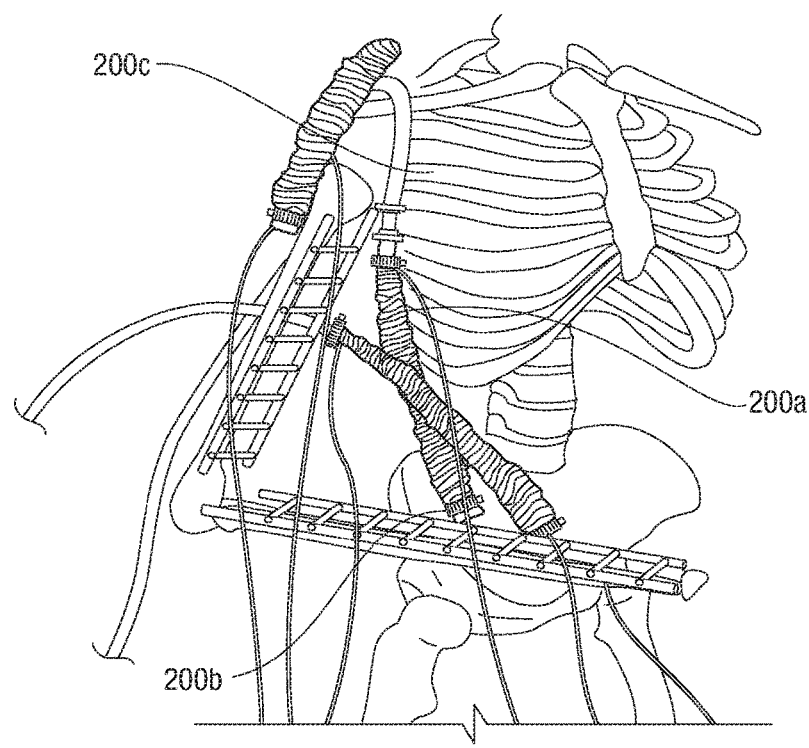
Figure 3D:
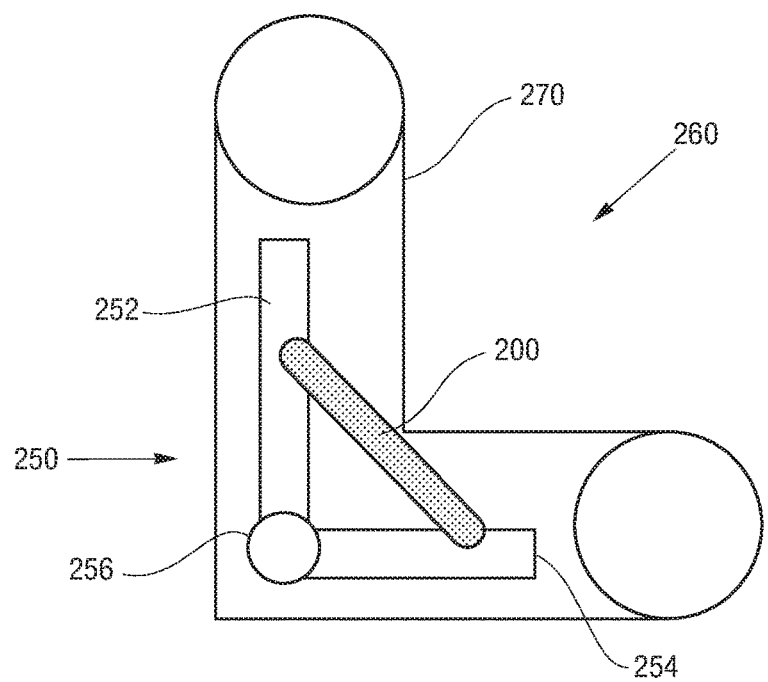
FIG. 3D illustrates an exoskeleton joint utilizing a lattice device according to the present disclosure.

In reference to FIG. 3A(i) and FIG. 3A(ii), FIG. 3B, FIG. 3C and FIG. 3D, the lattice device 250 powered by the actuator 200 may be employed as an exoskeleton. In some embodiments, the lattice device 250 may be provided about a user's joint (either internally or externally) to assist the user in moving the limbs of the joint.

For example, FIG. 3A(i) and FIG. 3A(ii) show the actuator 200 being attached to the lattice device 250 using fasteners 309. The position of the actuator attachment points on the lattice device may be varied up and down the latticed device 250, for example, to control the torque applied on the lattice device 250 by the actuator 200.

The fasteners 309 can include cutouts therethrough to assist in attaching the actuator 200 to the lattice device 250. In some embodiments, the fasteners 309 may be a thin sheet metal with cuts into approximately 1 inch by 3 inch pieces and then bent a third of the way down at a 90 degree angle. On one third of the piece, a hole can be drilled so that the cutout could be aligned, concentrically, between one or more adapters for the actuator 200 for a sturdy and permanent attachment. The other half of the cutout can be bent to look like a hook so that it could be fastened around any segment of the latticed device 250. Because of the malleability of the sheet metal, it may be possible to adjust the bend angle so that the open end of the actuator 200 and adapters can stay parallel to maintain the structural integrity of the elastic. At least one aspect to this design may allow for easy detachment and attachment at both ends of the fasteners so the actuator 200 could be arranged in a variety of configurations and at different points on the lattice device 250.

FIG. 3B shows the lattice device 250 fastened to a portion of the skeleton. In reference to FIG. 3C, multiple actuators 200a, 200b, and 200c may be integrated with the lattice device 250 to allow for a skeletal actuator model that can actuate many degrees of freedom. For example, an actuator 200 can be attached as a shoulder flexor of the skeleton so that the model can actuate with two degrees of freedom. In some embodiments, two actuators 200 may be employed to actuate the elbow joint of the skeleton, and a third actuator 200 can be used to actuate the shoulder of the skeleton.

In reference to FIG. 3D, to create an exoskeleton joint 260, the lattice device 250 may be combined with a wearable sleeve 270. When the user wears the sleeve 270 about a joint of the user, the members 252, 254 of the lattice device can be positioned substantially along the limbs of the user joint. In this manner, the movement of the lattice members 252, 254 by the actuator 200 may assist the movement of the limbs of the user. In some embodiments, the lattice members 252, 254 may be shaped to conform to the shape of the user's limbs for additional comfort. In some embodiments, multiple lattice devices may be incorporated into a wearable clothing to help movement of multiple joints of the user.

The actuator system of the present disclosure may include one or more sensors, which may, for example, allow sensing the position of a limb actuated by the actuator system. For example, when the actuator is used to function as a bicep, the angle of the fore arm with respect to the upper arm may be sensed. Still further the measurement of electric resistance of actuating fluid within elastic inner member can be utilized to accurately estimate the linear length of the actuator when inner member is fully extended in the radial direction.

Figure 4:
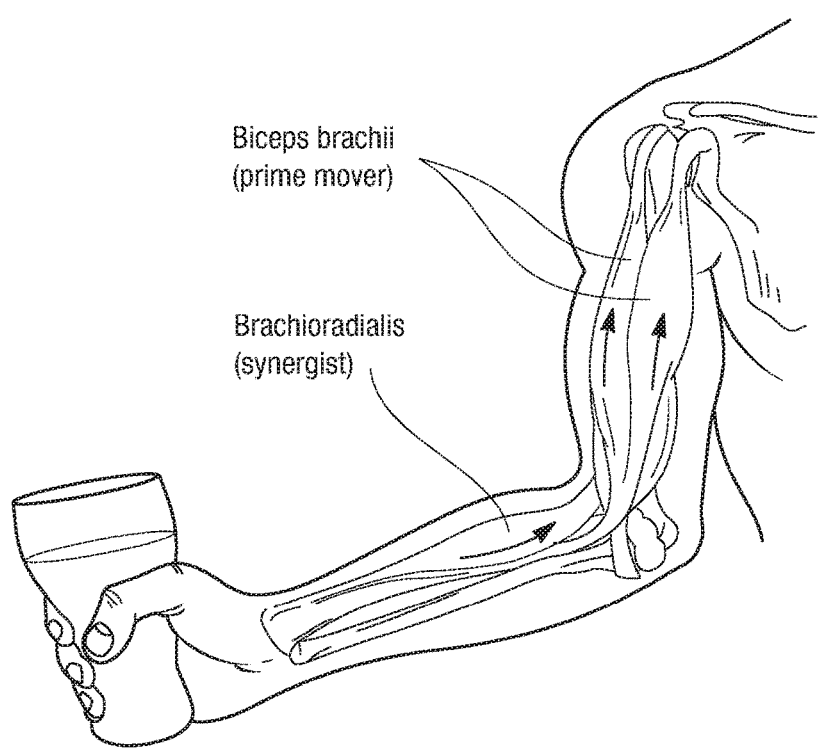
FIG. 4 illustrates a diagram of a muscle in a human arm, in particular, aspects of mimicking a muscle operation in a human arm.

FIG. 4 illustrates a diagram of a muscle in a human arm, in particular, aspects of mimicking a muscle operation in a human arm. There are various potential applications for the actuator systems of the present disclosure. For example, the actuator system can be used as exo-musculature and worn by people for various reasons, or it can be used in place of any rigid robotic actuator that currently exists. As exo-musculature, this design can be used in the health industry as a way to provide assistance and mobility to those that lack them, or it can be worn in order to augment a person's strength. There are a variety of uses for an exo-musculature design in the health industry. It can be used as prosthetics for people who have lost limbs. There are plenty of cases right now, where amputees are being given robotic limbs in place of their lost limbs. They have the ability now to control the movement of the robotic limb with their minds as accurately and as quickly as a human limb. The actuator system is more compliant than rigid robotics and has the potential to move more similarly to human limbs than rigid robotic limbs. The actuator system can be used in almost every aspect of physical therapy. It can be used to help a person regain movement after injuries. It can be used in the same manner to provide mobility and strength to people who have long been losing their mobility and strength. Because of its compliant nature, our hydraulic design would be much safer and much more applicable to human movement than any sort of rigid design.

Moreover, the actuator system of the present disclosure can also be used to provide augmented strength in other scenarios for humans and animals. Currently, the military is investing in powered, robotic exoskeletons in order to provide service men and women with super human strength. As advanced as these sorts of innovations are becoming, they have the same flaw in their rigidity as everything else. It is always going to have limitations in the degrees of freedom and mobility that comes with attaching another rigid structure to a human body. This design has the potential to produce the same large amounts of force as these military exoskeletons already do while being fluid and mobile and compliant enough to attach to a human body.

In some embodiments, the actuator system of the present disclosure can potentially be used instead of an electric motor for virtually any robotic need. Because the actuator system is extremely modular, it can be used anywhere from industrial robotics to the robots that kids tinker with as a hobby. This has the potential to help move robotics as a whole away from rigid structures to soft robotics.

Further, it is possible that the modular actuators can have embedded pressure sensors, elastic band length sensors, and conductive threads instead of conventional wiring.

In the context of orthotic devices and exo-skeletons the similarity that the actuators of the present disclosure have with human skeletal muscle can reduce the difficulty of their integration with exo-skeleton systems. The compliance that the actuators of the present disclosure can introduce into a joint, for example, that the actuators are easily adjustable over a wide range of spring constants, can reduce shock and jerk on both the mechanics of the exoskeleton and on the human operator.

Further, the hydraulically actuated actuators of the present disclosure can offer several advantages over a pneumatic actuation. For example, in the system of the present disclosure response times can be typically much faster, i.e. pressure propagates faster in water than in air, energy losses can be much smaller, and for incompressible fluids, output forces per unit area may be much larger enabling a more compact prime actuator for the same dynamic force output characteristics.

Referring to FIG. 5A and FIG. 5B(i) and FIG. 5B(ii), in some embodiments, the systems of the present disclosure may include multiple actuators 200 to provide a versatile system with sufficient degrees of freedom. Typically, each degree of freedom may require at least two ordinary solenoid on/off valves to control pressure in the actuators 200. However, having too many active valves in the system may be problematic due to consequences in cost, size, mass, and energy efficiency.

Referring to FIG. 5A, in order to minimize the number of valves and amount associated hardware, some embodiments of the present disclosure provide a multivalve system based on motorized rotary selector in series with fast active valve, which would significantly reduce the number of the required valves and hardware. In some embodiments, only two selectors and two active valves may be needed for the entire actuator array.

Still referring to FIG. 5A, a system 400 may include multiple actuators 200a-e connected in parallel. The system 400 may further include a selector having a rotary disc with a single outlet and a static disc with multiple openings, which correspond to degrees of freedom in one to one correspondence, as shown in FIG. 5B(i) and FIG. 5B(ii).

Only when the openings of the rotary and static disks are aligned and the fast valve is open fluid is allowed to flow through into the selected actuator 200.

For example, if fluid needs to be pumped into the n-th actuator, the selector on the inlet side of the system 400 may select the n-th opening and the selector's servo motor can align the rotary disk opening with the n-th tube. Then, the active valve can open and the pump can push the fluid into the n-th actuator. Fluid will pass through the active valve, the selector's opening and the passive valve before entering the actuator. Further, the passive valve may be a one way valve to prevent the fluid from flowing out of the actuator due to one-directional passive valve on the right.

When pressurized, the actuator can act to store energy in the form of elastic potential energy. This energy can be stored for an indefinite period of time. No effort is needed to maintain actuation state, but rather only to change it. When the n-th actuator is supplemented with the right amount of fluid, the active valve will close, and the selector will close too (disk opening will not be aligned with any of the tubes).

To release a desired amount of the fluid from the n-th actuator, the selector at the outlet of side of the system 400 on the right of FIG. 5A can align its disk opening with the n-th tube and the active valve will open. The fluid will move into the reservoir. Further, fluid won't be allowed to return to any of the actuators due to a one way passive valve on outlet of the actuator 200. In this manner, the same actuator is not engaged by the active elements on the input and output simultaneously. At least one advantage of the system 400 of the present disclosure is that it can only require two fast active solenoid valves for the entire actuator network. A conventional design would require two active valves per actuator; which would be costly, heavy, and bulky. A large number of passive valves as utilized in the disclosed design can be acceptable since they are typically inexpensive, very light and can be embedded within the tube with an inline arrangement.

Another potential advantage of the system 400 may be that actuators 200 can be actuated sequentially or simultaneously in parallel. For a task that does not require much force, a single actuator or a small number of actuators can be used, while others may be kept pressurized. Moreover, the system of the present disclosure allows use of multiple actuators sequentially to provide sufficient degree of freedom. The system also enables constant force to be maintained because while some actuators are being depressurized, others can be pressurized for the next operation. For a task requiring more force, additional actuators may be employed simultaneously. If further parallel actuations are desired, a more advanced approach could assume single pump and reservoir and a parallel configuration with multiple subsystems consisting of two or more active valves, selectors and actuator sub-networks.

Figure 6A:
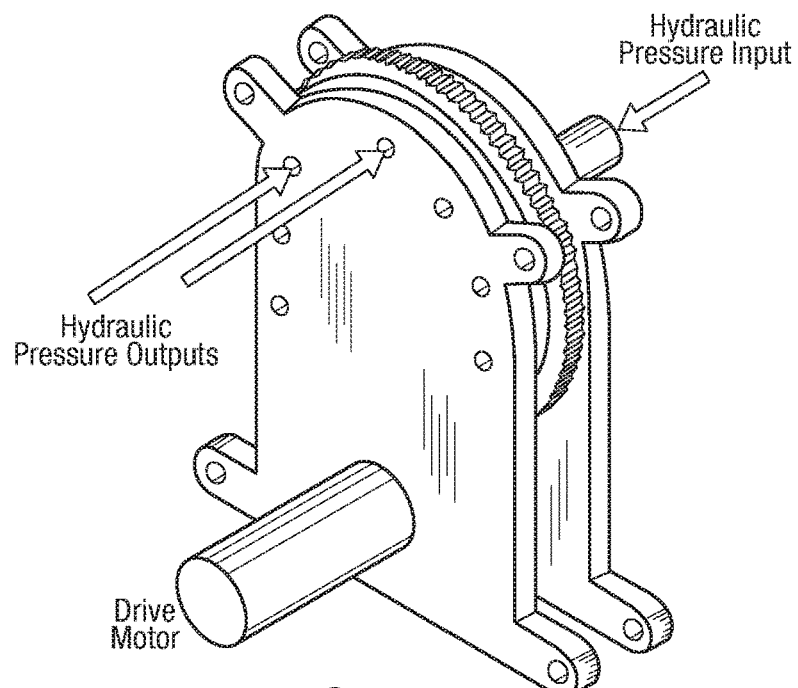
FIG. 6A and FIG. 6B show an actuator system according to the present disclosure.
Figure 6B:
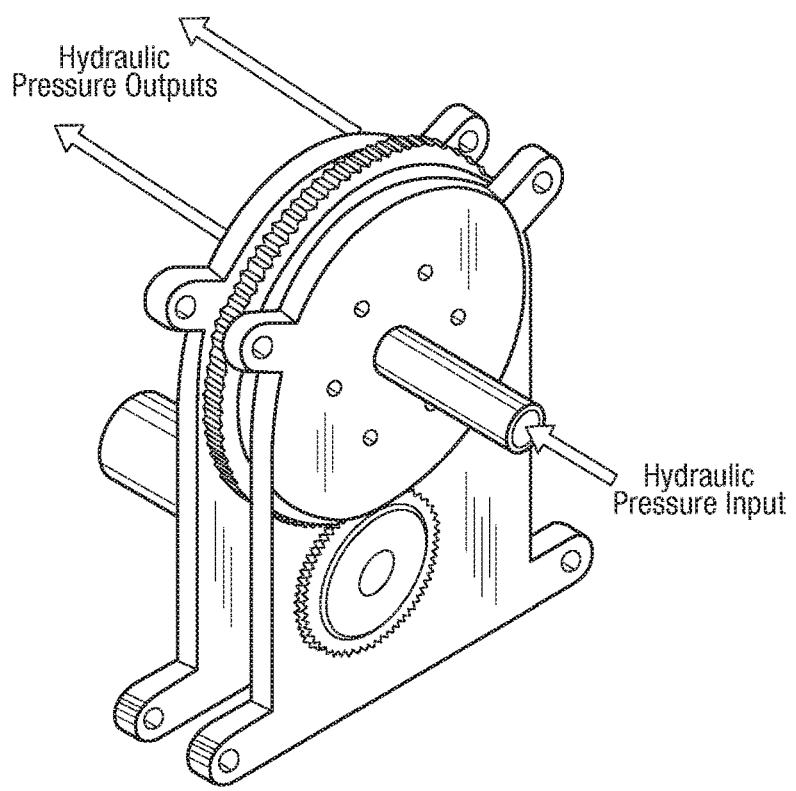

FIG. 6A and FIG. 6B show a conceptual view of an off-axial one-to-many valve selector. It is contemplated that some applications may have an actuator network that can require only very small flow rates, for example, only up to several cubic-centimeter-per-second. Further, such an implication can be that the hydraulic pump could be extremely compact and fast. Moreover, due to the inherent mechanical advantage properties of hydraulic systems, i.e. the input area being smaller than the output area, the mechanical loading on the pump can be engineered to be arbitrarily smaller than the loading on the actuator network. The servo-mechanism on the valve selector can be also compact and very fast. In other words, the drive motor may have a very high RPM that can be geared down to a range of speeds required by proposed application, as illustrated by the conceptual design depicted in FIG. 6A and FIG. 6B.

Figure 7A:
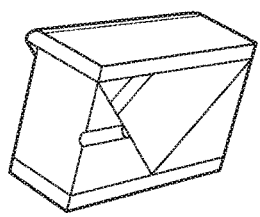
FIG. 7A(i)-FIG. 7A(v)
Figure 7A:
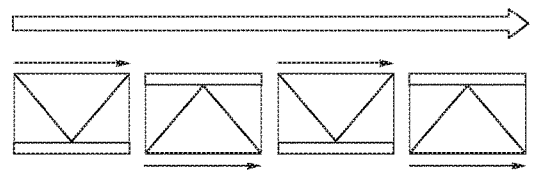
Figure 7A:
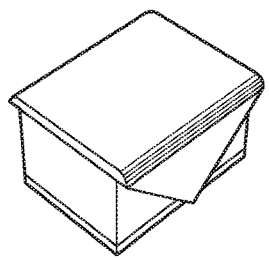
Figure 7A:
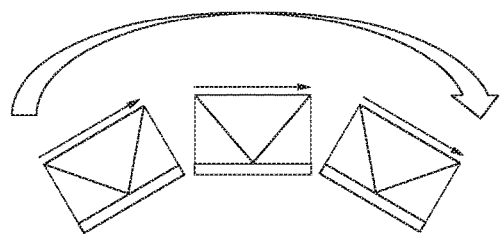
Figure 7A:
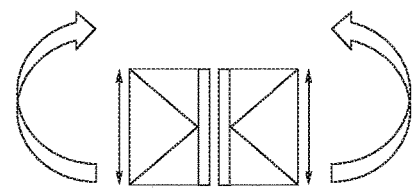
Figure 7B:
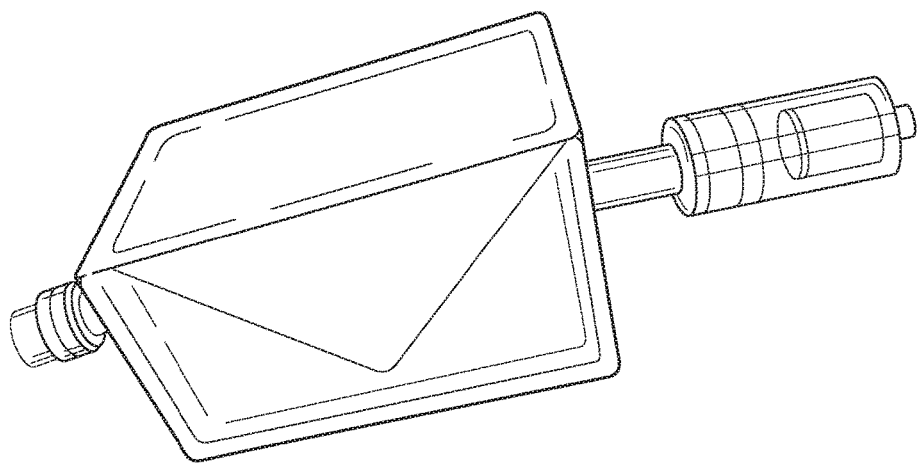
FIG. 7B and FIG. 7C show an actuator according to the present disclosure.
Figure 7C:
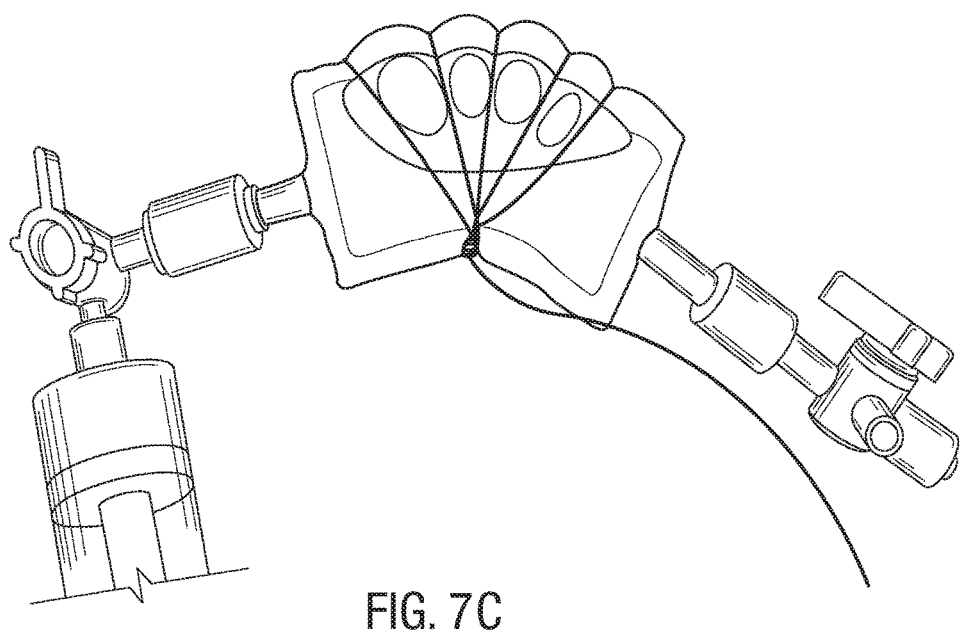

FIG. 7A(i)-FIG. 7A(v), FIG. 7B and FIG. 7C show modular hydraulically actuated units may have rectangular cross section and they can be fully biased to expansion along single side when pressurized. For example, these actuators disclosed in FIG. 7A(i)-FIG. 7C can be provided with a more complex 3D distribution of stiffness. It is possible that a skeletal structure can form a virtual joint as shown in FIG. 7C, wherein a string can be utilized to wrap units and constrain (only partially) radial expansion.

EXAMPLES

Prototypes

A. Prototype I

The first prototype was built with inexpensive, easily-accessible materials, such as common latex surgical tubing. One end of tube was sealed off by melting a small bit of latex on that end. On the other end, a barbed plastic connector was used to connect the actuator to a polyethylene tube. A small piece of polyester cloth was used as the inelastic outer wrap. A piece of the polyester fabric which measured approximately 15 in×3 in was sewn around the latex tube. The ends of the fabric were secured to the ends of the latex tube by using small pipe clamps on each end.

This first prototype could exert a maximum tensile force of about 25 N. However, Prototype I had some leaks, and that motivated need for the more robust Prototype II.

B. Prototype II

The second prototype was designed as a continuation of the first prototype. The elastic actuator used for the second prototype was the final design of the actuator. The design features a latex surgical tube on the inside and a polyester fabric on the outside. The actuator has a brass plug on the proximal end and a plastic adapter on the other end. The plug and the adapter are concentric and tightly installed. The fabric is attached to the tube with common metal hose clamps.

Latex was chosen for its exceptional resistance to wear and tear, high tensile strength, resilience, and elongation. The outer sleeve is made out of polyester and has an approximate length of 16 inches. It is ideal for this application as it is rigid, tough, and has low absorption of moisture. Additionally, it has a high flexural linear strength.

The pump used for the system is SHURflo 8035-963-239 12 Volts, direct current (VDC) diaphragm manual demand pump. It is a positive displacement, 3-chamber diaphragm pump that utilizes maximum discharge pressures to deliver high flow rates. The check valve is 2-way operational and prevents reverse flow while providing 6 ft head of forward flow. The pump was running at a discharge rate of 0.7 gallons-per-minute (GPM), which produced a pressure of 120 psi. The specified discharge range was chosen for safety purposes, as well as to make sure that the actuators receive a pressure of 30 psi after head loses.

The solenoid valves used for the system were plastic water solenoid valves 12 V, ½-inch nominal. The resting position was closed. The valve required 12 VDC supply across the terminals to open and allow flow in one direction. The gasket arrangement inside the valve requires a minimum pressure of 3 psi to operate. This is because they are one-way valves. The 3 psi of pressure keeps the valve closed. When the 12 V difference is sent to the solenoid, it forces the valve to remain open against the fluid flow.

The three exo-actuators were attached to a synthetic skeleton in order to display the use of the actuators as exo-musculature. As noted above, FIG. 4 is a diagram of the mimicked muscles. The actuators could not be directly connected to the bone of the skeletal model so a custom, latticed device was created. The device was attached to both the upper arm and forearm of the skeleton and allowed for the position of the actuator attachment points to be varied up and down the arm because of the lattice structure. Attachment of the actuators to lattice device itself was accomplished using rectangular sheet metal cutouts. The thin sheet metal was cut into approximately 1 in×3 in pieces and then bent a third of the way down at a 90° angle. On one third of the piece, the cutout was aligned between the adapters of the elastic actuator and polyurethane tubing for a sturdy and permanent attachment. The polyurethane tubing connected the exo-actuators to the valves. The other half of the cutout was bent as a hook so that it could be fastened around any segment of lattice structure that is desired. Finally, because of the malleability of the sheet metal, the bend angle was adjusted such that the open end of the actuator and adapters stayed parallel to maintain the structural integrity of the elastic. This design allowed for easy detachment and attachment at both ends so the actuators could be arranged in a variety of configurations.

The exo-musculature system was controlled by an Arduino Uno microprocessing board, based on the ATmega 328. The Arduino communicates with a computer via a USB cable. The Arduino Uno was programmed to control the solenoid valves based on instructions from the computer. The Arduino would listen to the keys pressed, and it then would open or close the valves depending on which key was pressed. The freeware, PuTTY, was utilized to interface between the computer and the Arduino. PuTTY was used to simply provide a bare, basic graphical user interface when controlling the Arduino.

To drive the valves, transistors were used to provide a 12-V supply to the solenoids. Specifically, six NPN bipolar junction transistors (BJTs) were used.

Experimental Results

A. Second Prototype: Constant Force Experiment

To test the final prototype, two types of test were performed. The actuator was suspended horizontally between two posts. One end of the actuator was held in place, while the other is tied to a string that runs over a pulley on the second post. Weights were tied at the end of the string to simulate the forces the actuator might experience during operation. For each experimental run, a different weight was attached. The actuator began in equilibrium at atmospheric pressure. For each data point, the actuator pressure was recorded from the internal pressure gauge, and the actuator length was measured. After each measurement, the valve between the actuator and running pump was opened for 50 ms. The process was repeated until the actuator was fully extended.

Figure 8:
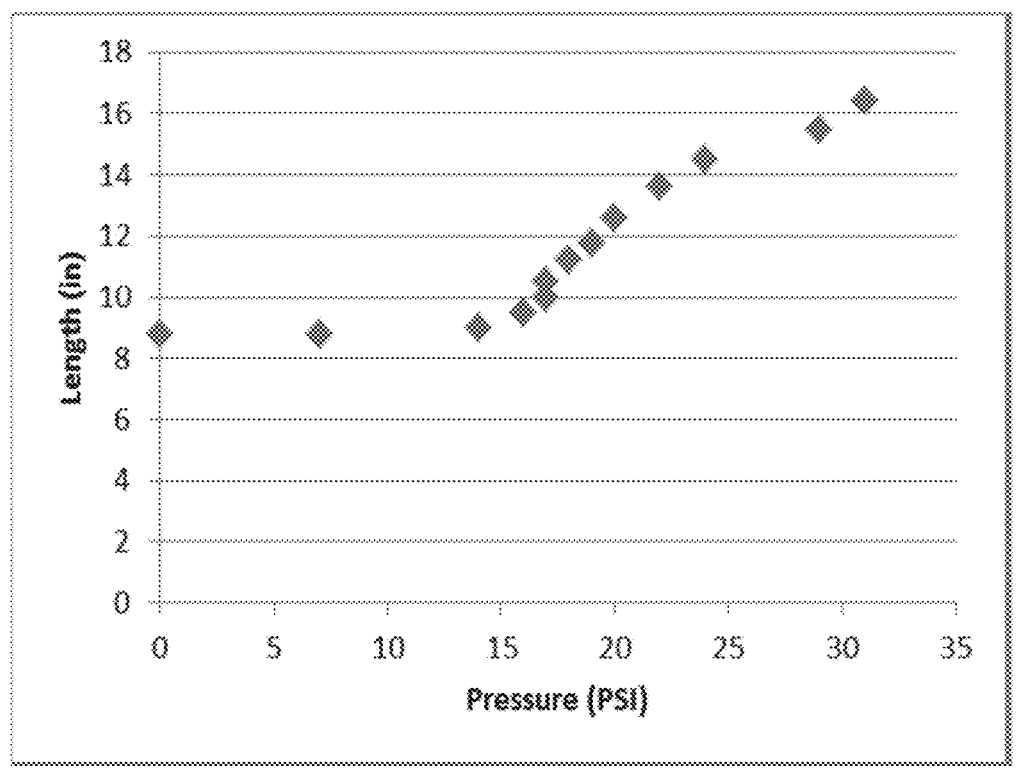
FIG. 8 and FIG. 9 are graph showing an actuator length relative to applied actuator pressure based on tests of a prototype actuator.
Figure 9:
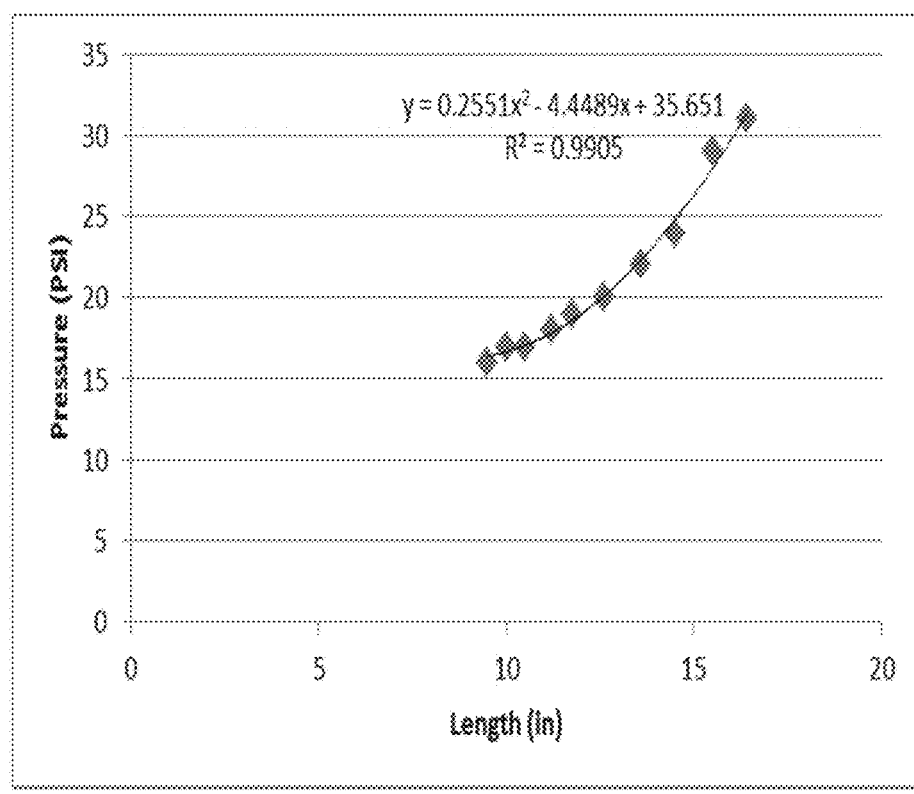

FIG. 8 shows the results of this experiment. The results of this experiment seem fairly linear after 15 PSI. FIG. 9 provides an inverted graph of the data, which shows a more accurate relation of pressure to length, in the form of a polynomial regression.

B. Second Prototype: Constant Length Experiment

For the constant length experiment, the actuator was once again suspended between the two posts, but this time both ends were affixed. At one end, there was a force sensor connected to Logger Pro. The actuator was stretched to several different lengths for each experimental run. The experiment began with the actuator stretched to the given length at atmospheric pressure. For each data point, the actuator pressure was recorded from the integrated pressure gauge and the force was read from Logger Pro. For each successive measurement, the valve between the actuator and running pump was opened for 50 ms of a second. This process was repeated until the actuator began to buckle and sag due to expansion (at which point the data became unreliable).

This experiment was used to find a relationship between force, length, and pressure. This experiment kept the length constant, while increasing the pressure.

Figure 10:
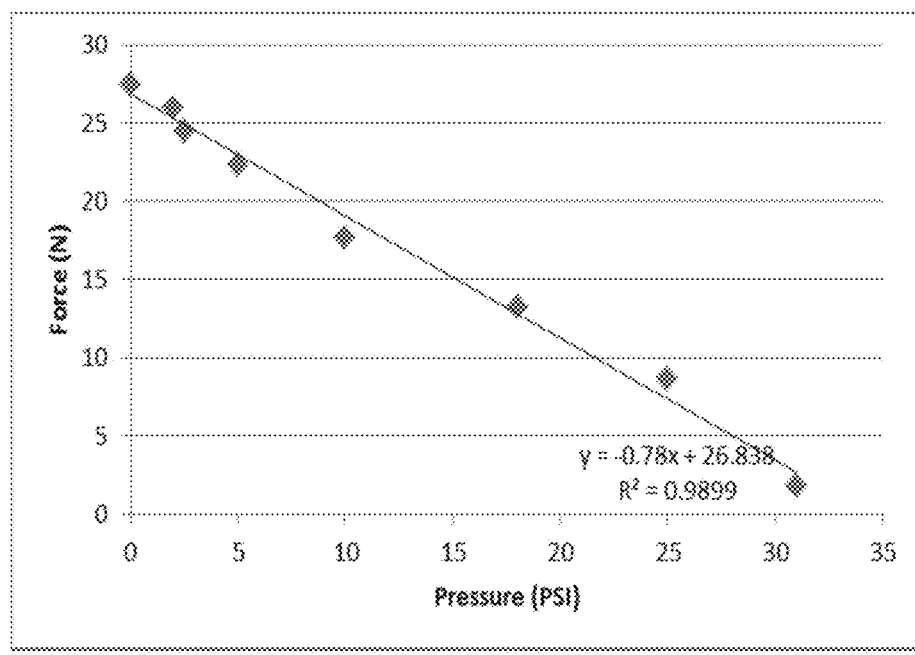
FIG. 10 is a graph of force relative to the pressure based on tests of a prototype actuator.

FIG. 10 shows that a linear relationship was found between the tensile force exerted by the actuator and the pressure inside the actuator. As the pressure inside increases, it produces an outward force on the actuator. This counteracts the tensile force produced by the actuator when it is in tension.

C. Actuator Resistance vs. Length

It was intended that the exo-actuator would use the internal resistance of the water to sense the length of the actuator.

Figure 11:
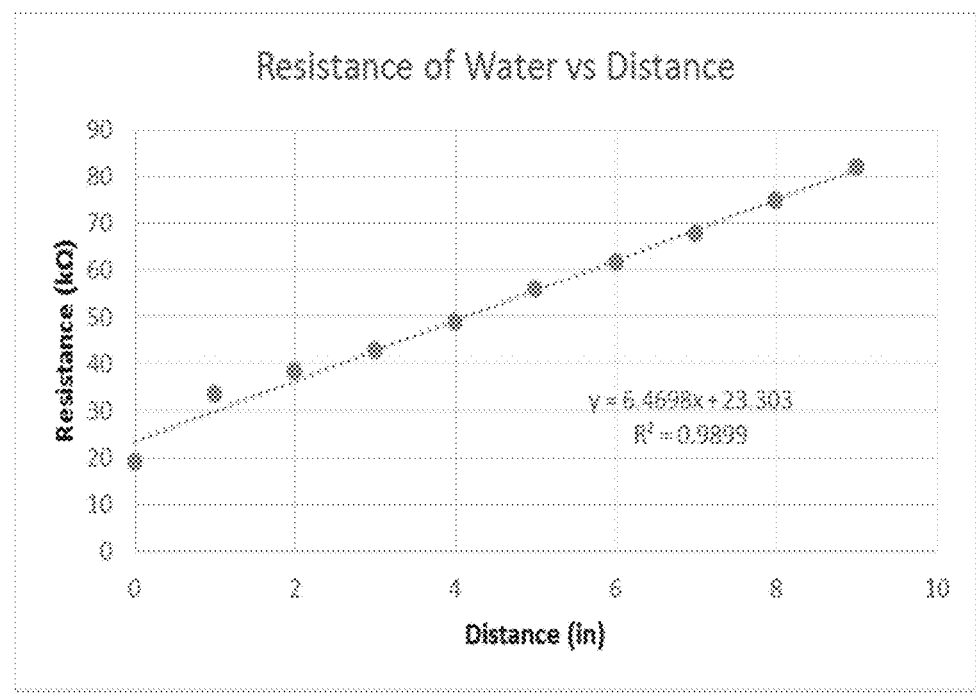
FIG. 11 is a graph of resistance relative to distance based on tests of a prototype actuator.

FIG. 11 shows a linear relationship between the distance between two probes submerged in water and the resistance measured across the two probes. This experiment was done to test the plausibility of using the conductivity of water to sense the length of the exo-actuator. The intent was to measure the resistance of the water within the latex tube in order to determine the length of the actuator.

Since there was a linear relationship between water resistance and distance, it was necessary to test this principle with the actual exo-actuator. The exo-actuator was iteratively filled with water. After every iteration the resistance of the water inside the latex tube was recorded along with the length of the exo-actuator.

While the initial experiment to determine the relationship between the conductivity of water and distance successfully showed that there was a linear correlation between the two, this experiment showed non-linear dependence between the range of actuator lengths and the exo-actuator's internal resistance. This is due to the actuator not being fully actuated when the elastic tube is expanding both radially and longitudinally, hence producing less reliable resistance readings.

Figure 12:
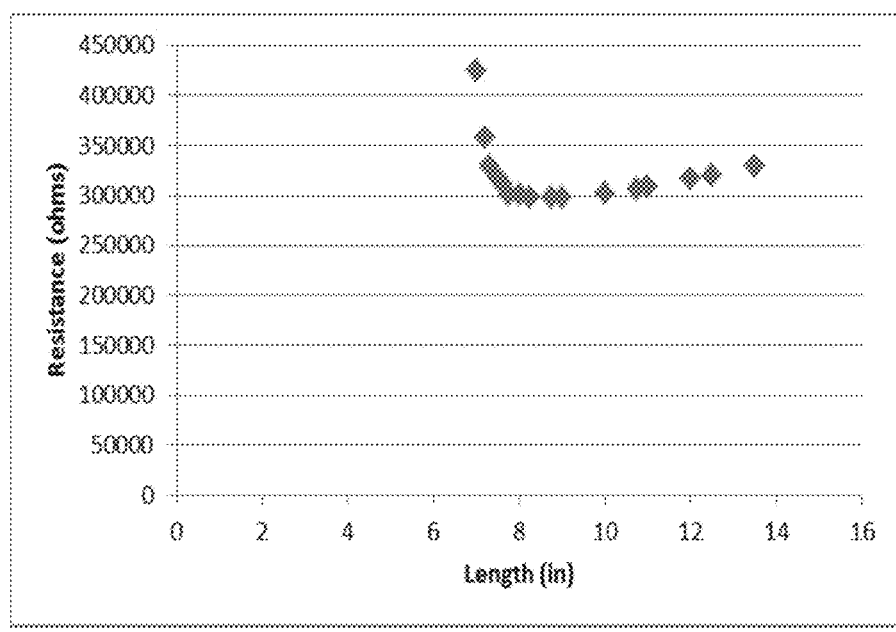
FIG. 12 and FIG. 13 are graphs of resistance relative to length based on tests of a prototype actuator.

FIG. 12 shows the data regarding the resistance of the water inside the exo-actuator at different lengths of the exo-actuator. The resistance seems to diminish at the start of the extension of the actuator, but then it steadily climbs upwards.

Figure 13:
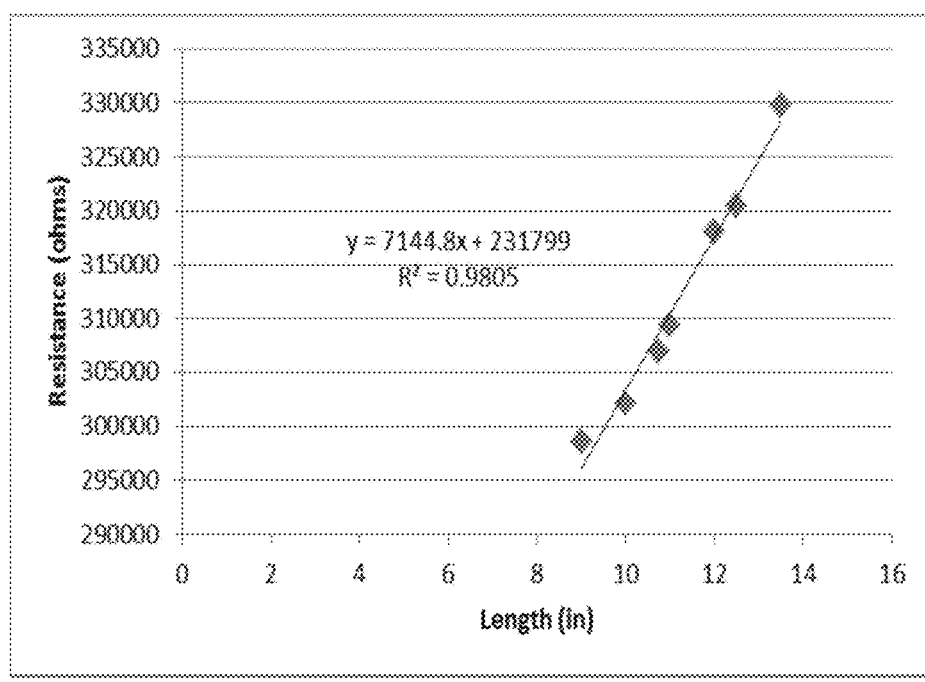

FIG. 13 shows that after the length of the actuator reaches a certain length (about nine inches), the increase in resistance is very linear. Between seven inches and nine inches, the elastic tube is expanding both radially and longitudinally. At the start of the expansion of the latex, its radial expansion is much larger than its longitudinal expansion. As the length approaches nine inches, the radial expansion decreases, and the longitudinal expansion increases. Once the length of the actuator is about nine inches, the latex tube can no longer expand radially at all, so the actuator only extends longitudinally after that. This accounts for the nonlinear decrease in resistance at the start and then the linear increase after nine inches.

In some embodiments, a hydraulically operated lattice device comprises a first member; a second member; and an actuator connected to the first member at its first end and to the second member at its second end, the actuator comprising an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state, wherein the movement of the actuator between the relaxed state and the expanded state cause a movement of at least one of the first member and the second member relative to the other member.

In some embodiments, an actuator system comprises a reservoir including an actuating fluid; and multiple actuators, each of the multiple actuators comprising: an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state; a pump in fluid communication with the reservoir and the actuators for selectively supplying the actuating fluid to the actuators; and a controller in communication with the pump to control operation of the pump.

In some embodiments, an exoskeleton joint comprises a wearable sleeve; a first member and a second member combined with the wearable sleeve, the second member being pivotably connected to the first member by a hinge; an actuator connected to the first member at its first end and to the second member at its second end, the actuator comprising an inner member made from an elastic material and defining a compartment for receiving an actuating fluid, the inner member being moveable in a longitudinal direction from a relaxed state to an expanded state by introducing an actuating fluid into the inner member; and an outer member made from an inelastic material and being disposed around the elastic inner member to control expansion of the elastic inner member in a radial direction, the outer member being moveable from a folded relaxed configuration to an unfolded extended configuration as the inner member moves from the relaxed state to the expanded state, wherein the movement of the actuator between the relaxed state and the expanded state cause a movement of at least one of the first member and the second member relative to the other member.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:
1. A lattice device comprising:
    a first member;
    a second member; and an actuator connected to the first member at a first end of the actuator and to the second member at a second end of the actuator, the actuator comprising:

an inner member made from an elastic material and having straight walls to define a straight, cylindrically shaped compartment for receiving an actuating fluid, the inner member being moveable in an axial direction from a relaxed state to an expanded state by introducing an actuating fluid into the inner member to pressurize the inner member; and an outer member being disposed immediately adjacent to and around the elastic inner member to control expansion of the elastic inner member in a radial direction, the outer member being inelastic in the radial direction and expandable in the axial direction as the inner member moves from the relaxed state to the expanded state, the outer member being formed from a sheet of material such that the outer member forms an uninterrupted barrier such that there are no opening in the outer member in the expanded state to prevent the inner member from protruding through the outer member, wherein, when the inner member is pressurized to move the inner member to its expanded state, the actuator expands in the axial direction, and wherein, when the inner member is de-pressurized to return the inner member to its relaxed state, the actuator contracts in the axial direction to cause a movement of at least one of the first member and the second member relative to the other member.

2. The lattice device of claim 1 wherein the outer member is connected to the elastic inner member discontinuously at one or more contact points.

3. The lattice device of claim 1 wherein the outer member is connected to the elastic inner member discontinuously at a first end and a second end.

4. The lattice device of claim 1 wherein the first member and the second member are pivotally connected by a hinge.

5. The lattice device of claim 1 wherein the actuator is axially symmetric.

6. The lattice device of claim 1 wherein the actuator is axially asymmetric having at least two segments with different elastic properties.

7. The lattice device of claim 1 wherein the outer member is configured to freely expand or contract in the axial direction along the inner member as the inner member moves between the relaxed state and the expanded state.

8. An actuator system comprising:
a reservoir including an actuating fluid; and
multiple actuators, each of the multiple actuators comprising:
an inner member made from an elastic material and having straight walls to define a straight, cylindrically shaped compartment for receiving an actuating fluid, the inner member being moveable in an axial direction from a relaxed state to an expanded state by introducing an actuating fluid into the inner member to pressurize the inner member; and
an outer member being disposed immediately adjacent to and around the elastic inner member to control expansion of the elastic inner member in a radial direction, the outer member being inelastic in the radial direction and expandable in the axial direction as the inner member moves from the relaxed state to the expanded state, the outer member being formed from a sheet of material such that the outer member forms an uninterrupted barrier such that there are no opening in the outer member in the expanded state to prevent the inner member from protruding through the outer member, wherein, when the inner member is pressurized to move the inner member to its expanded state, the actuator expands in the axial direction, and wherein, when the inner member is de-pressurized to return the inner member to its relaxed state, the actuator contracts in the axial direction to cause a movement of at least one of the first member and the second member relative to the other member; and a pump in fluid communication with the reservoir and the actuators for selectively supplying the actuating fluid to the actuators; and a controller in communication with the pump to control operation of the pump.

9. The actuator system of claim 8 wherein the outer member is connected to the elastic inner member discontinuously at one or more contact points.

10. The actuator system of claim 8 wherein the outer member is connected to the elastic inner member discontinuously at a first end and a second end.

11. The actuator system of claim 8 wherein the actuator is axially symmetric.

12. The actuator system of claim 8 wherein the actuator is axially asymmetric having at least two segments with different elastic properties.

13. The actuator system of claim 8 further comprising a rotary selector disposed between the pump and the actuators to enable the pump to selectively supply the actuating fluid to the actuators.

14. The actuator system of claim 8 wherein the outer member is configured to freely expand or contract in the axial direction along the inner member as the inner member moves between the relaxed state and the expanded state.

15. An exoskeleton joint comprising:
a wearable sleeve;
a first member and a second member combined with the wearable sleeve, the second member being pivotably connected to the first member by a hinge;
an actuator connected to the first member at a first end of the actuator and to the second member at a second end of the actuator, the actuator comprising:
an inner member made from an elastic material and having straight walls to define a straight, cylindrically shaped compartment for receiving an actuating fluid, the inner member being moveable in an axial direction from a relaxed state to an expanded state by introducing an actuating fluid into the inner member to pressurize the inner member; and
an outer member being disposed immediately adjacent to and around the elastic inner member to control expansion of the elastic inner member in a radial direction, the outer member being inelastic in the radial direction and expandable in the axial direction as the inner member moves from the relaxed state to the expanded state, the outer member being formed from a sheet of material such that the outer member forms an uninterrupted barrier such that there are no opening in the outer member in the expanded state to prevent the inner member from protruding through the outer member, wherein, when the inner member is pressurized to move the inner member to its expanded state, the actuator expands in the axial direction, and wherein, when the inner member is de-pressurized to return the inner member to its relaxed state, the actuator contracts in the axial direction to cause a movement of at least one of the first member and the second member relative to the other member.

16. The exoskeleton joint of claim 15 wherein the outer member is connected to the elastic inner member discontinuously at one or more contact points.

17. The exoskeleton joint of claim 15 wherein the outer member is connected to the elastic inner member discontinuously at a first end and a second end.

18. The exoskeleton joint of claim 15 wherein the actuator is axially asymmetric having at least two segments with different elastic properties.

19. The of exoskeleton joint of claim 15 wherein the outer member is configured to freely expand or contract in the axial direction along the inner member as the inner member moves between the relaxed state and the expanded state.

20. A lattice device comprising:
a first member;
a second member; and
an actuator connected to the first member at a first end of the actuator and to the second member at a second end of the actuator, the actuator comprising:
an inner member made from an elastic material and having straight walls to define a straight, cylindrically shaped compartment for receiving an actuating fluid, the inner member being moveable in an axial direction from a relaxed state to an expanded state by introducing an actuating fluid into the inner member to pressurize the inner member; and
an outer member being disposed immediately adjacent to and around the elastic inner member to control expansion of the elastic inner member in a radial direction, the outer member being inelastic in the radial direction and expandable in the axial direction as the inner member moves from the relaxed state to the expanded state,
wherein, when the inner member is pressurized to move the inner member to its expanded state, the actuator expands in the axial direction, and
wherein, when the inner member is de-pressurized to return the inner member to its relaxed state, the actuator contracts in the axial direction to cause a movement of at least one of the first member and the second member relative to the other member, and
wherein the outer member is made of a foldable material such that:
when the inner member moves from its expanded state to its relaxed state, the outer member freely folds onto itself to create a plurality of free form folds, wherein at least some of the folds of the plurality of free form folds form one or more overlaps with one another, and
when the inner member moves to its expanded state, the plurality of folds of the outer member unfold to enable the outer member to expand in the axial direction.

* * * * *